US012797586B2

(12) United States Patent
Wang et al.

(10) Patent No.: US 12,797,586 B2
(45) Date of Patent: Nov. 17, 2026

(54) DRUG BALLOON CATHETER CAPABLE OF CONTROLLING DRUG RELEASE AND USE THEREOF

(71) Applicant: SHANGHAI BIO-HEART BIOLOGICAL TECHNOLOGY CO., LTD., Shanghai (CN)

(72) Inventors: Philip Li Wang, Shanghai (CN); Tao Cai, Shanghai (CN); Junyi Wang, Shanghai (CN); Hanyang Liu, Shanghai (CN); Chenzhao Zhang, Shanghai (CN)

( * ) Notice: Subject to any disclaimer, the term of this patent is extended or adjusted under 35 U.S.C. 154(b) by 538 days.

(21) Appl. No.: 18/241,255

(22) Filed: Sep. 1, 2023

(65) Prior Publication Data

US 2024/0226509 A1 Jul. 11, 2024

Related U.S. Application Data

(63) Continuation of application No. PCT/CN2023/071402, filed on Jan. 9, 2023.

(51) Int. Cl.
*A61M 25/10* (2013.01)
*A61L 29/08* (2006.01)

(52) U.S. Cl.
CPC ........... *A61M 25/10* (2013.01); *A61L 29/085* (2013.01); *A61M 2025/105* (2013.01)

(58) Field of Classification Search
CPC ............ A61M 25/10; A61M 2025/105; A61M 25/1002; A61M 2025/1075;
(Continued)

(56) References Cited

U.S. PATENT DOCUMENTS 6,753,071 B1 6/2004 Pacetti
2005/0163913 A1* 7/2005 Spencer .................. A61L 27/34 427/2.1
(Continued)

FOREIGN PATENT DOCUMENTS

CN 102781488 A 11/2012
CN 110292701 A 10/2019
CN 111317907 A 6/2020

OTHER PUBLICATIONS

Jin, J., et al., "Effects of Molecular Weight of Blocks on in vitro Degradation and Drug Release Performance of PLGA-mPEG Microparticle", Journal of Chemical Engineering of Chinese Universities, 1003-9015(2008)05-0785-06, vol. 22, Issue No. 5, pp. 785-790, (Oct. 2008).
(Continued)

*Primary Examiner* — Wesley G Harris
*Assistant Examiner* — Neeraja Gollamudi

(57) ABSTRACT

The present application provides a novel drug balloon catheter capable of controlling drug release, comprising a balloon, a catheter, and a drug coating, and wherein a surface of the balloon is coated with the drug coating, and the drug coating is divided into a first drug coating, a second drug coating, and a third drug coating; and release rates of a drug in the first drug coating, the second drug coating, and the third drug coating are different. By controlling a drug release period, a problem of a toxic reaction caused by a downstream blood vessel is solved, while the drug release period is prolonged, thereby effectively treating a blood vessel tear caused by over-dilation and improving a long-term effectiveness of a drug treatment.

6 Claims, 1 Drawing Sheet

(58) Field of Classification Search
CPC ......... A61M 25/104; A61M 2205/0238; A61L 29/085; A61L 2300/416; A61L 29/16; A61L 2300/41; A61L 2300/602; A61L 2300/608
See application file for complete search history.

(56) References Cited

U.S. PATENT DOCUMENTS

| | | | | |
|---|---|---|---|---|
| 2005/0246009 | A1* | 11/2005 | Toner ........................ | A61P 9/14 623/1.42 |
| 2007/0142897 | A1 | 6/2007 | Consigny et al. | |
| 2008/0195079 | A1 | 8/2008 | Moore et al. | |
| 2011/0251663 | A1* | 10/2011 | Melder ..................... | A61F 2/91 623/1.42 |
| 2015/0196690 | A1 | 7/2015 | Stankus et al. | |
| 2019/0009063 | A1* | 1/2019 | Cottone .............. | A61M 25/104 |
| 2019/0358439 | A1 | 11/2019 | Michal et al. | |
| 2021/0259976 | A1* | 8/2021 | Wang ................... | A61K 9/4816 |
| 2022/0016398 | A1* | 1/2022 | Li ......................... | A61M 25/10 |

OTHER PUBLICATIONS

Lin, W-J, et al., "Pegylated Polyester Polymeric Micelles as a Nano-carrier: Synthesis, Characterization, Degradation, and Biodistribution", Journal of Experimental and Clinical Medicine, https://shorturl.at/R8zLb, vol. 2, Issue No. 01, pp. 4-10, (Feb. 2010).
Zhang, K., et al., "PEG-PLGA Copolymers: Their Structure and Structure-Influenced Drug Delivery Applications", Journal of Controlled Release, https://doi.org/10.1016/j.jconrel.2014.03.026, vol. 183, pp. 77-86, (Jun. 10, 2014).

* cited by examiner

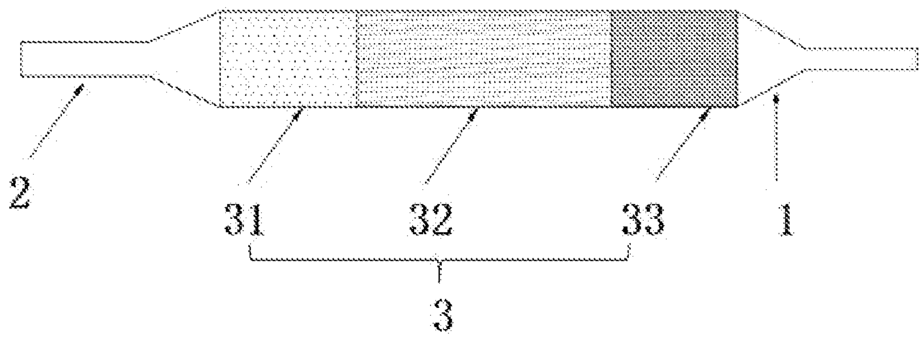
2
31
32
33
1
3

DRUG BALLOON CATHETER CAPABLE OF CONTROLLING DRUG RELEASE AND USE THEREOF

CROSS-REFERENCE TO RELATED APPLICATIONS

The present application is a continuation of International Application No. PCT/CN2023/071402, with an international filing date of Jan. 9, 2023, which is based upon and claims priority to Chinese Patent Application No. 202211631220.5, filed on Dec. 19, 2022, the entire contents of all of which are incorporated herein by reference.

FIELD OF TECHNOLOGY

The present disclosure relates to the technical field of medical devices, A61F2/958, and especially relates to a novel drug balloon catheter capable of controlling drug release and use thereof.

BACKGROUND

Nowadays, cardiovascular diseases have become the most fatal killer threatening human health, and are mainly manifested by angiostenosis, thereby causing insufficient blood supply to a part of organs, loss of original functions and even blocking of a blood vessel to cause a life risk. At present, the most common treatment method for the cardiovascular diseases is a percutaneous transluminal angioplasty. At present, a drug eluting stent and a drug balloon are mainly used. The drug balloon conveys an antiproliferative drug to a blood vessel lesion area by a balloon catheter in a minimally invasive intervention manner. The drug on the balloon is transferred to an inner wall of a blood vessel through a balloon expansion. Under a dual effect of the balloon expansion and the antiproliferative drug, a purpose of treating angiostenosis is achieved. Hyperproliferation of a smooth muscle cell may be effectively inhibited, a restenosis occurrence rate is reduced, a stent does not need to be placed, and a bleeding risk is small.

Since a shape and a size of the blood vessel in human body are important data before and after a treatment, according to an analysis of clinical imaging data, the blood vessel of the human body presents a cone shape, diameters of a near end and a far end of the blood vessel in a lesion area are inconsistent, if an expansion diameter of the balloon is expanded according to the end with a larger size of the blood vessel, the end with a smaller size of the blood vessel is tom due to overexpansion, and the blood vessel is damaged. Besides, a release rate of a drug coating in the existing drug balloon is relatively single, and thus in a certain period of time, more drugs are accumulated at a downstream of the blood vessel, which may cause a toxic reaction of the blood vessel. When the release rate is great, a toxic reaction is aggravated, but when the release rate is too slow, a concentration of an active drug in a lesion area is low, and an effect of inhibiting stenosis is weak. In addition, the drug coating on a surface of the drug balloon is easily washed in a blood washing environment, such that a treatment effect of the balloon on the lesion part is reduced. If the coating contains more particles and has a larger size, a potential risk of blocking the blood vessel may be caused.

Chinese patent CN108378964A discloses a drug balloon, which reduces drug poisoning by spraying drug coatings with different drug-loading densities on a surface of the balloon. Chinese patent CN107670163A discloses a drug balloon dilating catheter, and a preparation method therefor and use thereof. In the technology, by spraying coatings with different drug-loading doses to a near end and a far end of the balloon, although a degree of uneven drug concentration distribution in the blood vessel in a short time is reduced, the technology needs to strictly control the spraying process of the drug coating. Besides, a fixation effect of the drug is small, the duration in the blood is short, and a treatment effect is not durable. In the above two patents, although the doses on the surface of the balloon are not consistent, a drug release period is consistent. The drug at the downstream of the blood vessel is increased rapidly in a certain period of time, the toxic reaction of the blood vessel is still caused, and after a certain period of time, the dose at a tom part of the blood vessel is reduced, and the treatment effect is reduced.

SUMMARY

In order to solve the above technical problems, the present disclosure firstly provides a novel drug balloon catheter capable of controlling drug release. By controlling a drug release period, a problem of a toxic reaction caused by a downstream blood vessel is solved, while the drug release period is prolonged, thereby effectively treating a blood vessel tear caused by over-dilation and improving a long-term effectiveness of a drug treatment.

Further, the drug balloon catheter comprises a balloon 1, a catheter 2, and a drug coating 3, wherein a surface of the balloon 1 is coated with the drug coating 3, and the drug coating 3 is divided into a first drug coating 31, a second drug coating 32, and a third drug coating 33.

Further, the catheter 2 is arranged on both sides of the balloon 1, and the catheter 2 is connected with two top ends of the balloon 1.

Further, the first drug coating 31, the second drug coating 32, and the third drug coating 33 are horizontally arranged in parallel along the surface of the balloon 1, so as to divide the surface of the balloon 1 into a three-stage structure.

Preferably, release rates of a drug in the first drug coating 31, the second drug coating 32, and the third drug coating 33 are different.

Further, the drug coating 3 comprises the following raw materials: an active drug, an adhesive, a sustained-release agent, and a polyol substance.

Further, the drug coating comprises the following raw materials in parts by weight: 20-100 parts of the active drug, 10-80 parts of the adhesive, 5-65 parts of the sustained-release agent, and 5-70 parts of the polyol substance.

Preferably, the drug coating 3 comprises the following raw materials in parts by weight: 20-80 parts of the active drug, 10-70 parts of the adhesive, 5-60 parts of the sustained-release agent, and 5-60 parts of the polyol substance.

Further, the active drug is used for inhibiting smooth muscle cell proliferation, reducing intimal hyperplasia, reducing incidence of restenosis and inflammatory response, including but not limited to, any one or a combination of more of rapamycin, paclitaxel, zotarolimus, heparin, hirudin, aspirin, dexamethasone, and a derivative thereof.

Preferably, the active drug is selected from any one or a combination of more of rapamycin, paclitaxel, heparin, hirudin, and a derivative thereof.

Further, in the drug coating, the loading amount of the active drug is 1-10 $\mu g/mm^2$.

Further, the adhesive is used for increasing an adhesion of a drug to a blood vessel, inhibiting a loss of an active drug caused by blood washing, and improving a treatment effect and a durability of the drug to the blood vessel.

Further, the adhesive is selected from at least one of an ester substance, an amide substance, liposome, a carboxylic acid substance, and a polyhydroxy substance.

Further, the ester substance is selected from any one or a combination of more of a copolymer of PEG and hyaluronic acid, a polylactic acid-glycolic acid (PLGA) copolymer, a block copolymer of PEG and PLGA, polylactide, polysorbate, polyhydroxyalkanoate, polylactic acid, polyvinyl acetate, a polyhydroxybutyrate valerate copolymer, and a sebacic acid copolymer.

Further, the amide substance is selected from any one or a combination of more of iopromide, polyvinylpyrrolidone, polyamide, chitosan modified polyamide, an amino acid, N-[3-(2-dibutylaminoethyl)-1H-indol-5-yl]naphthalene-1-sulfonamide, and N-[3-(2-diethylaminoethyl)-1H-indol-5-yl]-trans-β-styrene sulfonamide, preferably, iopromide.

Further, the carboxylic acid substance is selected from any one or a combination of more of tannic acid, shellac, hyaluronic acid, and a salt thereof.

Further, the polyhydroxy substance is selected from any one or a combination of more of PEG, chitosan, and cyclodextrin.

Further, the liposome is selected from one or a combination of more of soybean phospholipid, lecithin, cholesterol, cephalin, distearoyl phosphatidylcholine, dimyristoyl phosphatidylcholine, and a modified substance thereof.

In a preferred embodiment, the liposome is soybean phospholipid or cholesterol.

Further, in the drug coating, the sustained-release agent is any one or a combination of more of an mPEG-PLGA copolymer, poly-3-hydroxybutyrate, a hydroxybutyrate-hydroxyvalerate copolymer, sodium alginate hydrogel, chitosan, cellulose, pectin, and alkyl glycoside.

Preferably, the sustained-release agent is any one or a combination of more of an mPEG-PLGA copolymer, a hydroxybutyrate-hydroxyvalerate copolymer, and sodium alginate hydrogel.

In a preferred embodiment, the sustained-release agent is an mPEG-PLGA copolymer.

Further, in the mPEG-PLGA copolymer, a number-average molecular weight of mPEG is 4,000-90,000, and a number-average molecular weight of PLGA is 1,000-150,000.

Further, in the mPEG-PLGA copolymer, a number-average molecular weight of the mPEG is 5,000-80,000, and a number-average molecular weight of the PLGA is any one or a combination of more of 1,000-3,000, 3,000-5,000, 5,000-10,000, 50.000-70,000, and 100,000-120,000.

Preferably, in the mPEG-PLGA copolymer, a number-average molecular weight of the mPEG is 5,000-60,000, and a number-average molecular weight of the PLGA is 5,000-10,000, 50,000-70,000, and 100,000-120,000.

Further, with respect to the first drug coating, the second drug coating, and the third drug coating, the number-average molecular weights of the PLGAs in the mPEG-PLGA copolymers are all different.

In the present application, the active drug is wrapped by a long molecular chain of the mPEG-PLGA copolymer, an intermolecular hydrogen bond or a conjugation is generated on a polar group and an annular structure in the active drug through a polar group such as —NH—, —O—, —OH, C═O and the like in the mPEG-PLGA copolymer. The active drug is fixed in a cross-linking structure formed by the mPEG-PLGA copolymer, molecular weights of mPEG and PLGA in the mPEG-PLGA copolymer molecule are adjusted to regulate and control a cross-linking degree of the structure, and thus a drug release rate is further regulated and controlled. When the molecular weight of the PLGA is too large, the mPEG-PLGA copolymer needs more energy to degrade, a residence time of the active drug on a blood vessel wall is longer, a drug release concentration in a short time is low, and a treatment effect on a blood vessel tearing injury is poor. But when the molecular weight is too small, the active drug is not sufficiently wrapped by a cross-linked molecular chain of the mPEG-PLGA copolymer, the active drug easily flows along with blood, the residence time on the blood vessel wall is short, the drug release amount in a short time is large, and an effect is not lasting. Based on this, the present application further stipulates that the mPEG-PLGA copolymers used in the first drug coating, the second drug coating, and the third drug coating in the drug balloon have different molecular weights, so as to regulate and control the drug release rate and the release period in the first drug coating, the second drug coating, and the third drug coating, improve a sustained-release effect of a drug, prolong effective treatment time, and avoid a toxic reaction of a blood vessel.

Further, the number-average molecular weights of the PLGA in the mPEG-PLGA copolymers in the first drug coating, the second drug coating, and the third drug coating are not strictly regulated, and the number-average molecular weights of the PLGAs in the mPEG-PLGA copolymers in the three coatings are only required to be kept inconsistent, such that the coating on the drug balloon has 24 combination modes and may be configured according to calcification and tear of the blood vessel.

In one embodiment, in the first drug coating of the balloon catheter, a number-average molecular weight of the PLGA in the mPEG-PLGA copolymer is 5,000-10,000; in the second drug coating, a number-average molecular weight of the PLGA in the mPEG-PLGA copolymer is 50,000-70,000; in the third drug coating, a number-average molecular weight of the PLGA in the mPEG-PLGA copolymer is 100,000-120,000; and the third coating (i.e. an end of the mPEG-PLGA copolymer with a large number-average molecular weight) is placed at an end with a serious tearing of a blood vessel.

In one embodiment, in the first drug coating of the balloon catheter, a number-average molecular weight of the PLGA in the mPEG-PLGA copolymer is 50,000-70,000; in the second drug coating, a number-average molecular weight of the PLGA in the mPEG-PLGA copolymer is 5,000-10,000; in the third drug coating, a number-average molecular weight of the PLGA in the mPEG-PLGA copolymer is 100,000-120,000; and the third coating (i.e. an end of the mPEG-PLGA copolymer with a large number-average molecular weight) is placed at an end with a serious tearing of a blood vessel.

In one embodiment, in the first drug coating of the balloon catheter, a number-average molecular weight of the PLGA in the mPEG-PLGA copolymer is 100,000-120,000; in the second drug coating, a number-average molecular weight of the PLGA in the mPEG-PLGA copolymer is 5,000-10,000; in the third drug coating, a number-average molecular weight of the PLGA in the mPEG-PLGA copolymer is 50,000-70,000; and the third coating is placed at an end with a serious tearing of a blood vessel and may also be placed according to needs.

Further, the polyol substance is selected from any one or a combination of more of polyvinyl alcohol, mannitol, sorbitol, xylitol, resveratrol, and pentaerythritol.

Preferably, the polyol substance is the polyvinyl alcohol with a number-average molecular weight of 5,000-60,000, further preferably, 8,000-30,000.

Further, preparation methods for the first drug coating, the second drug coating, and the third drug coating are all as follows: dissolving coating raw materials in an organic solvent, and uniformly mixing same; and preparing the mixture into a microsphere shape by an ultrasonic treatment, and spraying the microsphere on a surface of a balloon.

Further, the organic solvent comprises, but is not limited to, at least one of ethanol, glycerol, isopropanol, diethyl ether, acetone, ethyl acetate, and ethyl formate.

Further, the organic solvent accounts for 30-80% of a total mass of the organic solvent and the coating raw materials.

Further, the microsphere has an average diameter of less than 10 μm, preferably 0.05-8 μm.

Further, a structure of the drug balloon is not specifically limited in the present application, and the drug balloon is common on the market.

Further, a form of the drug balloon catheter is not specifically limited in the present application, and the drug balloon catheter comprises, but is not limited to, any one of OTW or RX.

Further, the drug balloon catheter of the present application is used in dilating a blood vessel.

Beneficial Effects

1. The balloon catheter provided by the present application may control drug release period under a condition of unchanged drug content, solves a problem of a toxic reaction caused by a downstream blood vessel, further effectively prolongs the drug release period of a torn part of the blood vessel, avoids tearing caused by excessive dilation of the blood vessel, may effectively inhibit proliferation of a vascular smooth muscle cell, reduces a probability of restenosis, and relieves an inflammatory reaction.
2. In the drug balloon of the present application, three coatings are designed, drug release rates of each coating are inconsistent, a molecular weight of an mPEG-PLGA copolymer in the sustained-release agent of the drug coatings is further controlled, a drug release degree in each coating is controlled, an adhesion and retention time of a drug on a blood vessel wall is prolonged, and the tom part of the blood vessel is continuously treated.
3. In the coatings of the present application, the sustained-release agent may effectively wrap an active drug, and regulates and controls a release rate. The adhesive may produce an intermolecular action with the active drug, and relies on a functional group to increase the adhesion to the blood vessel wall. The polyol substance has a good hydrophilicity, and may activate the coatings to release the inside drug. A combined action of each component in the coating raw materials is utilized to effectively control the release amount of the drug and an adhesive ability of the blood vessel wall the drug, and reduce a drug loss produced by blood washing. The balloon has an excellent treatment effect on a tom position of the blood vessel.

BRIEF DESCRIPTION OF THE DRAWINGS

FIG. 1 is a schematic diagram of the drug balloon catheter of the present disclosure.

DESCRIPTION OF THE EMBODIMENTS

Examples

Example 1

The example provided a drug balloon catheter. The drug balloon catheter comprised a balloon 1, a catheter 2, and a drug coating 3, wherein a surface of the balloon 1 was coated with the drug coating 3, and the drug coating 3 was divided into a first drug coating 31, a second drug coating 32, and a third drug coating 33.

The first drug coating 31 comprised the following raw materials in parts by weight: 50 parts of rapamycin, 40 parts of soybean phospholipid, 30 parts of an mPEG-PLGA copolymer, and 30 parts of PEG; a number-average molecular weight of the PEG was 20,000; a number-average molecular weight of mPEG in the mPEG-PLGA copolymer was 32,000, and a number-average molecular weight of PLGA was 8,000; and the drug loading amount of the first drug coating was 4 μg/mm$^2$.

The second drug coating 32 comprised the following raw materials in parts by weight: 60 parts of rapamycin, 50 parts of soybean phospholipid, 20 parts of an mPEG-PLGA copolymer, and 20 parts of PEG; a number-average molecular weight of the PEG was 20,000; a number-average molecular weight of mPEG in the mPEG-PLGA copolymer was 32,000, and a number-average molecular weight of PLGA was 60,000; and the drug loading amount of the second drug coating was 5 μg/mm$^2$.

The third drug coating 33 comprised the following raw materials in parts by weight: 50 parts of rapamycin, 40 parts of soybean phospholipid, 20 parts of an mPEG-PLGA copolymer, and 30 parts of PEG; a number-average molecular weight of the PEG was 20,000; a number-average molecular weight of mPEG in the mPEG-PLGA copolymer was 32,000, and a number-average molecular weight of PLGA was 110,000; and the drug loading amount of the third drug coating was 4 μg/mm$^2$.

Preparation methods for the first drug coating, the second drug coating, and the third drug coating were all as follows: respective raw materials of each coating were dissolved in ethyl acetate, wherein a mass of the raw materials accounted for 50% and a mass of the ethyl acetate solution accounted for 50%, the materials were uniformly mixed, the mixture was prepared into a microsphere shape by an ultrasonic treatment, wherein the microsphere had an average diameter of 3 μm, and the microsphere was sprayed on a set position of a surface of a balloon.

A measurement standard of the above parts by weight was consistent.

Example 2

The example provided a drug balloon catheter. The drug balloon catheter comprised a balloon 1, a catheter 2, and a drug coating 3, wherein a surface of the balloon 1 was coated with the drug coating 3, and the drug coating 3 was divided into a first drug coating 31, a second drug coating 32, and a third drug coating 33.

The first drug coating 31 comprised the following raw materials in parts by weight: 20 parts of rapamycin, 10 parts of soybean phospholipid, 5 parts of an mPEG-PLGA copolymer, and 5 parts of PEG; a number-average molecular weight of the PEG was 30.000; a number-average molecular weight of mPEG in the mPEG-PLGA copolymer was 5,000, and a number-average molecular weight of PLGA was 50,000; and the drug loading amount of the first drug coating was 2 μg/mm$^2$.

The second drug coating 32 comprised the following raw materials in parts by weight: 60 parts of rapamycin, 50 parts of soybean phospholipid, 30 parts of an mPEG-PLGA copolymer, and 30 parts of PEG; a number-average molecular weight of the PEG was 5,000; a number-average molecular weight of mPEG in the mPEG-PLGA copolymer was 5,000, and a number-average molecular weight of PLGA was 10,000; and the drug loading amount of the second drug coating was 6 μg/mm$^2$.

The third drug coating 33 comprised the following raw materials in parts by weight: 80 parts of rapamycin, 70 parts of soybean phospholipid, 60 parts of an mPEG-PLGA copolymer, and 60 parts of PEG; a number-average molecular weight of the PEG was 10,000; a number-average molecular weight of mPEG in the mPEG-PLGA copolymer was 60,000, and a number-average molecular weight of PLGA was 120,000; and the drug loading amount of the third drug coating was 8 μg/mm$^2$.

Preparation methods for the first drug coating, the second drug coating, and the third drug coating were all as follows: respective raw materials of each coating were dissolved in ethyl acetate, wherein a mass of the raw materials accounted for 70% and a mass of the ethyl acetate solution accounted for 30%, the materials were uniformly mixed, the mixture was prepared into a microsphere shape by an ultrasonic treatment, wherein the microsphere had an average diameter of 8 μm, and the microsphere was sprayed on a set position of a surface of a balloon.

A measurement standard of the above parts by weight was consistent.

Example 3

The example provided a drug balloon catheter. The drug balloon catheter comprised a balloon 1, a catheter 2, and a drug coating 3, wherein a surface of the balloon 1 was coated with the drug coating 3, and the drug coating 3 was divided into a first drug coating 31, a second drug coating 32, and a third drug coating 33.

The first drug coating 31 comprised the following raw materials in parts by weight: 30 parts of rapamycin, 10 parts of soybean phospholipid, 15 parts of an mPEG-PLGA copolymer, and 10 parts of PEG; a number-average molecular weight of the PEG was 10,000; a number-average molecular weight of mPEG in the mPEG-PLGA copolymer was 10,000, and a number-average molecular weight of PLGA was 100,000; and the drug loading amount of the first drug coating was 3.5 μg/mm$^2$.

The second drug coating 32 comprised the following raw materials in parts by weight: 40 parts of rapamycin, 30 parts of soybean phospholipid, 30 parts of an mPEG-PLGA copolymer, and 5 parts of PEG; a number-average molecular weight of the PEG was 5,000; a number-average molecular weight of mPEG in the mPEG-PLGA copolymer was 20,000, and a number-average molecular weight of PLGA was 5,000; and the drug loading amount of the second drug coating was 6 μg/mm$^2$.

The third drug coating 33 comprised the following raw materials in parts by weight: 70 parts of rapamycin, 50 parts of soybean phospholipid, 60 parts of an mPEG-PLGA copolymer, and 50 parts of PEG; a number-average molecular weight of the PEG was 8,000; a number-average molecular weight of mPEG in the mPEG-PLGA copolymer was 40,000, and a number-average molecular weight of PLGA was 50,000; and the drug loading amount of the third drug coating was 6 μg/mm$^2$.

Preparation methods for the first drug coating, the second drug coating, and the third drug coating were all as follows: respective raw materials of each coating were dissolved in ethyl acetate, wherein a mass of the raw materials accounted for 20% and a mass of the ethyl acetate solution accounted for 80%, the materials were uniformly mixed, the mixture was prepared into a microsphere shape by an ultrasonic treatment, wherein the microsphere had an average diameter of 0.05 μm, and the microsphere was sprayed on a set position of a surface of a balloon.

A measurement standard of the above parts by weight was consistent.

The PEG and the mPEG-PLGA copolymers were both purchased from Evonik.

Performance Test Method:

Animal experiment to verify sustained-release effect of drugs prepared from mPEG-PLGA with different molecular weights: an animal model of mini-pigs was used, drugs prepared from mPEG-PLGAs of different molecular weights were used in the animal model of pigs respectively, and time nodes were set at 0 day (instant), 30 days, 60 days, and 90 days. A pig blood vessel was taken and subjected to a drug detection.

Experimental subject: the model of mini-pigs, weighed 25-45 kg.

Experimental product: drug balloons prepared from the mPEG-PLGA with different molecular weights with a drug content of 6 μg/mm$^2$.

Experimental Solution:

(1) The animal model of 4 pigs was selected to respectively correspond to the time nodes of 0 day (instant), 30 days, 60 days, and 90 days. The experimental products with a number-average molecular weight of the PLGA at 60,000, 8,000, and 110,000 were implanted into cardiac blood vessel RCA, LCX, and LAD of the animal model of pigs respectively.

(2) The corresponding pigs were sacrificed at the time nodes of 0 day (instant), 30 days, 60 days, and 90 days, and the blood vessel was taken for detecting the drug content. A detection result was characterized by a ratio of the release amount of the drug on the blood vessel wall to the drug on the surface of the balloon before implantation. The result was shown in Table 1.

The result of the performance test.

TABLE 1

| Days | 0 day | 30 days | 60 days | 90 days |
|---|---|---|---|---|
| RCA (60000) | 15.68% ± 10.5% | 92.12% ± 5.5% | 93.23% ± 4.5% | 97.18% ± 1.8% |
| LCX (8000) | 17.15% ± 12.5% | 94.45% ± 5.6% | 95.45% ± 4.7% | 98.12% ± 1.4% |
| LAD (110000) | 12.13% ± 9.5% | 90.12% ± 6.5% | 92.34% ± 5.6% | 96.52% ± 2.8% |

It can be known from the above results, when a number-average molecular weight of the PLGA in the mPEG-PLGA was greater, a sustained-release effect on the drug was better. When the mPEG-PLGA was used in the drug coating of the balloon catheter, the drug release rate may be effectively reduced, the drug release rate of the balloon catheter was different, a timely drug administration treatment of an early-stage blood vessel tearing may be realized, and a later-stage drug sustained release may be realized to achieve a continuous treatment effect, and the drug coating may not cause a toxic reaction of a blood vessel.

What is claimed is:

1. A novel drug balloon catheter capable of controlling drug release, comprising: a balloon, a catheter, and a drug coating, wherein a surface of the balloon is coated with the drug coating, and the drug coating is divided into a first drug coating, a second drug coating, and a third drug coating; and release rates of a drug in the first drug coating, the second drug coating, and the third drug coating are different, the first drug coating, the second drug coating, and the third drug coating are horizontally arranged in parallel along a surface of the balloon so as to divide the surface of the balloon into a three-stage structure; each of the first drug coating, the second drug coating, and the third drug coating comprises a sustained-release agent of an mPEG-PLGA copolymer, wherein in the mPEG-PLGA copolymer, mPEG has a number-average molecular weight of 5,000-80,000, and PLGA has a number-average molecular weight of 1,000-3,000, 3,000-5,000, 5,000-10,000, 50,000-70,000, 100,000-120,000 or a combination thereof, wherein with respect to the first drug coating, the second drug coating, and the third drug coating, the number-average molecular weights of the PLGAs in the mPEG-PLGA copolymers are all different.

2. The drug balloon catheter according to claim 1, wherein the drug coating comprises the following raw materials: an active drug, an adhesive, a sustained-release agent, and a polyol substance.

3. The drug balloon catheter according to claim 2, wherein the drug coating comprises the following raw materials in parts by weight: 20-100 parts of the active drug, 10-80 parts of the adhesive, 5-65 parts of the sustained-release agent, and 5-70 parts of the polyol substance.

4. The drug balloon catheter according to claim 3, wherein in the drug coating, the loading amount of the active drug is 1-10 $\mu g/mm^2$.

5. The drug balloon catheter according to claim 2, in the drug coating, the adhesive is selected from at least one of an ester substance, an amide substance, and a liposome.

6. Use of the drug balloon catheter according to claim 1 in dilating a blood vessel.

* * * * *